US005770232A

United States Patent [19]
Sizer et al.

[11] Patent Number: 5,770,232
[45] Date of Patent: Jun. 23, 1998

[54] METHOD OF DISINFECTING THE FOOD CONTACT SURFACES OF FOOD PACKAGING MACHINES AND DISINFECTING SOLUTION THEREFOR

[75] Inventors: Charles S. Sizer, Hawthorne Woods; Ronald W. Swank, Crystal Lake, both of Ill.

[73] Assignee: Tetra Laval Holdings & Finance, SA, Pully, Switzerland

[21] Appl. No.: 811,136

[22] Filed: Mar. 3, 1997

Related U.S. Application Data

[63] Continuation of Ser. No. 687,791, Jul. 19, 1996, abandoned, which is a continuation of Ser. No. 317,385, Oct. 4, 1994, abandoned.

[51] Int. Cl.$^6$ .................................................. A01N 39/02
[52] U.S. Cl. .......................... 424/616; 424/606; 424/615
[58] Field of Search ................................... 424/606, 615, 424/616

[56] References Cited

PUBLICATIONS

Roundy, Z.D., Our Industry Today: Treatment of Milk for Cheese with Hydrogen Peroxide, Dairy Sci., 41, 1460 (1958).
Curran, Harold R., et al., The Sporicidal Action of Hydrogen Peroxide and the Use of . . . , J. Bacteriol, 40, 523 (1940).
Nambudripad, V.K.N., et al., Bactericidal Efficiency of Hydrogen Peroxide, Ind. J. Dairy Sci., 2, 65 (1949).
Swartling, P., et al. The Sterilizing Effect Against Bacillus Subtilis spores . . . , J. Dairy Res.,35,423 (1968).
Stevenson, K.E. et al., Bacterial Spore Resistance to Hydrogen Peroxide, Food Technology, Nov. 1983, all pgs.
I. Van Bockelmann and B. Von Bockelmann, *The Sporicidal Action of Hydrogen Peroxide–A Literature Review*, 1wt__ report, vol. 5, No. 6 (1972).
New Push for Aseptics, Modern Packaging, Nov. 1971.
James R. Russo and Robert Bannar, *Aseptic Packaging: How far will it go?*, Food Engineering, Mar. 1981.
Q.J. Smith and K.L. Brown, *The resistance of dry spores of Bacillus subtilis var. globigii (NCIB 8058) to solutions of hydrogen peroxide in relation to aseptic packaging*, J. Fd Technol., vol. 15, 169–179 (1980.
R. T. Toledo, F.E. Escher and J.C. Ayres, *Sporicidal Properties of Hydrogen Peroxide Against Food Spoilage Organisms*, Applied Microbiology, vol. 26, No. 4, pp. 592–597 (1973).
Stanley E. Wallen and Homer W. Walker, *Resistance of Spores of Bacillus subtilis var. Niger Produced From Subcultures of Spores Surviving Hydrogen Peroxide Exposure*, Journal Of Food Protection, vol. 43, Jul. 1980.
Cal Andres, *FDA approval opens way for aseptic packaging of shelf–stable milk, juices in U.S.*, Food Processing, Mar. 1981.
James Wang and Romeo T. Toledo, *Sporicidal Properties of Mixtures of Hydrogen Peroxide Vapor and Hot Air*, Food Technology, Dec. 1986.
A G Perkin, *Hydrogen peroxide & aseptic packaging*, Mar. 1982.
Rees B. Davis and Dennis M. Dignan, *Use of Hydrogen Peroxide Sterilization in Packaging Foods*, Association of Food and Drug Officials Quarterly, vol. 47:12, 1983.
K.E. Stevenson and B.D. Shafer, *Bacterial spore resistance to hydrogen peroxide*, Food Technology, Nov. 1983.

*Primary Examiner*—Brian M. Burn
*Attorney, Agent, or Firm*—Michael A. Catania

[57] ABSTRACT

A method of disinfecting the food contact surfaces of a food packaging machine comprises introducing to the machine an aqueous solution comprising from about 0.1% to about 1% by weight of hydrogen peroxide and from about 0.01% to about 0.1% by weight of sodium acid pyrophosphate. The food contact surfaces are contacted with the solution at a temperature of at least about 70° C. for a time period of at least about 15 minutes.

8 Claims, 9 Drawing Sheets

METHOD OF DISINFECTING THE FOOD CONTACT SURFACES OF FOOD PACKAGING MACHINES AND DISINFECTING SOLUTION THEREFOR

This is a continuation of application Ser. No. 08/687,791, filed Jul. 19, 1996 now abandoned which is a continuation of application Ser. No. 08/317,385 filed Oct.4,1994 now abandoned.

TECHNICAL FIELD

The present invention relates to food packaging machines. In particular, the present invention relates to an improved method of disinfecting the interior food contact surfaces of food packaging machines and to the disinfecting solution used in the improved method.

BACKGROUND

Hydrogen peroxide ($H_2O_2$) has been employed as a bactericidal and sporicidal agent for several decades. The use of hydrogen peroxide for the sterilization of pipes, filters, and other food processing components has been reported as early as 1916. Hydrogen peroxide is also employed as a bleaching agent and antimicrobial agent in the manufacture of certain foods.

Among the chemical sterilants available for use in connection with food processing and packaging equipment, hydrogen peroxide is among the most suitable. Hydrogen peroxide decomposes into water and oxygen, both of which are generally considered harmless in moderate quantities. Thus, small residues of hydrogen peroxide on the food contact surfaces of food packaging equipment, as well as on the packaging material and in the product itself, can generally be tolerated without adverse effects on health and safety. Moreover, hydrogen peroxide does not generally impart an off-flavor to a food product.

The U.S. Food and Drug Administration has approved the use of hydrogen peroxide as a sterilant on inert food contact surfaces, such as metal and glass, under the provisions of 21 CFR 178.1005. That regulation provides that hydrogen peroxide solution may be safely used to sterilize food contact surfaces, and defines hydrogen peroxide solution as being an aqueous solution containing not more than 35% hydrogen peroxide by weight. Under 21 CFR 178.1005, hydrogen peroxide solution may also contain optional adjuvant substances generally recognized as safe in or on food.

The sporicidal action of hydrogen peroxide has been studied extensively. Plotted survivor curves of the type shown in FIG. 1, for spores of Bacillus stearothermophilus and other bacilli, indicate that the destruction of these spores in hydrogen peroxide is semilogarithmic. While several researchers have reported straight-line survivor curves, some curves show pronounced shoulders while others show a tailing of survivor curves for spores of several bacilli.

The destruction of spores by hydrogen peroxide is also influenced by other factors, namely, hydrogen peroxide concentration, temperature, pH, the presence of other ionic constituents, treatment with ultrasonic waves, treatment with ultraviolet radiation, and the inherent resistance of spores to hydrogen peroxide. In the disinfection of food contact surfaces, the primary factors are hydrogen peroxide concentration, temperature, and pH.

Figure 1:
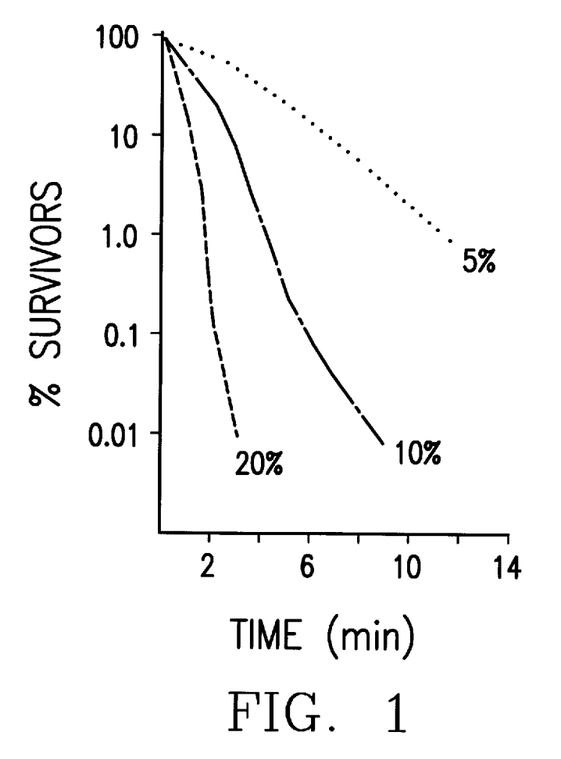
FIG. 1 is a plot of the effect of hydrogen peroxide concentration on the destruction of *Bacillus stearothermophilus*.

At low concentrations, hydrogen peroxide solutions have generally been found to be bactericidal but not highly sporicidal. As shown in FIG. 1, the sporicidal efficacy of hydrogen peroxide has been found to increase with increasing concentration. To obtain rapid sporicidal activity, relatively high concentrations of hydrogen peroxide have traditionally been employed in disinfecting solutions, typically about 35% hydrogen peroxide by weight. In concentrated form, however, hydrogen peroxide can generate substantial volumes of oxygen, creating a fire or explosion hazard, even at room temperature.

Figure 2:
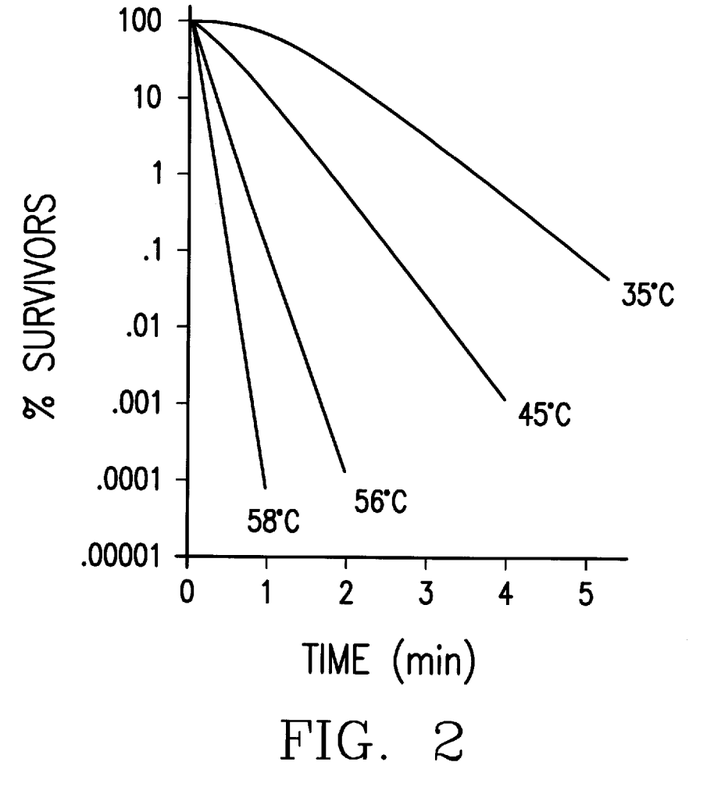
FIG. 2 is a plot of the effect of temperature on the destruction of *Bacillus subtilis* spores in 25.8% hydrogen peroxide.

The temperature of hydrogen peroxide solutions also has a pronounced effect on the rate of spore destruction. Hydrogen peroxide is not rapidly sporicidal at room temperature. As shown in FIG. 2, the rate of spore destruction increases as the temperature of a 25.8% $H_2O_2$ solution is increased.

The effect of pH on spore destruction is less pronounced than the effects of concentration and temperature. Some researchers have reported that hydrogen peroxide was more highly sporicidal under acidic conditions.

Traditional methods of disinfecting the food contact surfaces of food packaging machines generally involved the following steps:

(a) Pre-rinsing the food contact surfaces with water at a temperature of 50°–60° C. for about 8–10 minutes;

(b) Contacting the food contact surfaces with an alkali solution, typically 1.0–1.5% NaOH by weight, with a minimum pH of 13.0, at a temperature of 80°–85° C. for about 15–20 minutes;

(c) Rinsing the alkali solution from the food contact surfaces with water at room temperature for about 5–8 minutes;

(d) Contacting the food contact surfaces with an acid solution, typically 0.6–1.2% $HNO_3$ or $H_3PO_4$ by weight, with a maximum pH of 1.5, at a temperature of 60°–70° C. for about 10–15 minutes;

(e) Rinsing the acid solution from the food contact surfaces with an aqueous solution of 0.2–0.35% peracetic acid (hydrogen peroxide and acetic acid) by weight (commercially available under the trade name OXONIA) at room temperature for about 15–20 minutes;

(f) Contacting the food contact surfaces with water at a temperature of 90°–95° C. for about 25–30 minutes; and (g) Contacting the food contact surfaces with an aqueous solution of 0.2–0.35% peracetic acid by weight at 35°–40° C. for about 25–30 minutes.

Peracetic acid is generally recognized as being an effective bactericide and fungicide for food processing equipment. However, peracetic acid is extremely corrosive on the metal components of food processing equipment, as well as on the sealing components like rubber gaskets. Moreover, peracetic acid has a strong odor which becomes more noxious as its temperature increases. Thus, the temperature of peracetic acid must generally be maintained below about 40° C. to avoid excessive coffosiveness and the evolution of noxious odors. At temperatures below about 40° C., however, the efficacy of peracetic acid as a sporicidal agent is significantly reduced.

An aqueous solution containing 35% hydrogen peroxide and 0.03% sodium acid pyrophosphate ("SAPP") by weight is commercially available from the Klenzade division of Ecolab Inc. under the trade name "one-step/pre-stabilized" OXY-PAK. Such a 35% $H_2O_2$/0.03% SAPP solution cannot be used as a substitute for peracetic acid in the traditional disinfecting method described above because the solution is a relatively ineffective sporicidal agent at temperatures around 35°–40° C. At temperatures above about 70° C., the 35% $H_2O_2$/0.03% SAPP solution evolves unacceptably large amounts of oxygen. When diluted to form an aqueous solution of 0.1–1.0% $H_2O_2$/0.0001–0.001% SAPP, the hydrogen peroxide is more unstable and the conductivity of the solution is so reduced, based upon the presence of only trace amounts of SAPP, that concentration monitoring and metering of the solution is impeded. Inadequate stabilization of the hydrogen peroxide results in a breakdown of the peroxide into water and oxygen.

The metal ions and chlorine normally present in city water or well water greatly reduce the efficacy of hydrogen peroxide as a bactericidal agent, especially at low concentrations. Gerhardt and Marquis (1994) and Shin et al. (1994) have demonstrated that divalent cations such as $Fe^{++}$ have a protective effect on the killing of bacteria with hydrogen peroxide.

SUMMARY OF THE INVENTION

An improved method of disinfecting the food contact surfaces of a food packaging machine comprises:
(a) introducing to the machine an aqueous solution comprising from about 0.1% to about 1% by weight of hydrogen peroxide and from about 0.01% to about 0.1% by weight of sodium acid pyrophosphate;
(b) contacting the food contact surfaces with the solution at a temperature of at least about 70° C. for a time period of at least about 15 minutes;
(c) removing substantially all of the solution from the machine.

In the preferred method, the contacting temperature ranges from about 90° C. to about 100° C. The preferred contacting time period is at least about 30 minutes. The most preferred contacting time period is about 30 minutes.

The method preferably further comprises, between steps (b) and (c), cooling the solution to room temperature within the machine while the solution remains in contact with the food contact surfaces. The solution is preferably removed by introducing to the machine food to be packaged.

An improved aqueous solution for disinfecting the food contact surfaces of a food packaging machine comprises from about 0.1% to about 1% by weight of hydrogen peroxide and from about 0.01% to about 0.1% by weight of sodium acid pyrophosphate.

Another improved solution for disinfecting the food contact surfaces of a food packaging machine consists essentially of from about 0.1% to about 1% by weight of hydrogen peroxide, from about 0.01% to about 0.1% by weight of sodium acid pyrophosphate, and the balance water.

DETAILED DESCRIPTION OF THE PREFERRED EMBODIMENTS

Turning first to FIG. 1, a plot of the effect of hydrogen peroxide concentration on the destruction of *Bacillus stearothermophilus* illustrates the traditional view that the sporicidal efficiency of hydrogen peroxide increases with increasing concentration.

In FIG. 2, a plot of the effect of temperature on the destruction of *Bacillus subtilis* spores in 25.8% hydrogen peroxide illustrates that the rate of spore destruction increases as the temperature of the hydrogen peroxide solution is increased.

Figure 3:
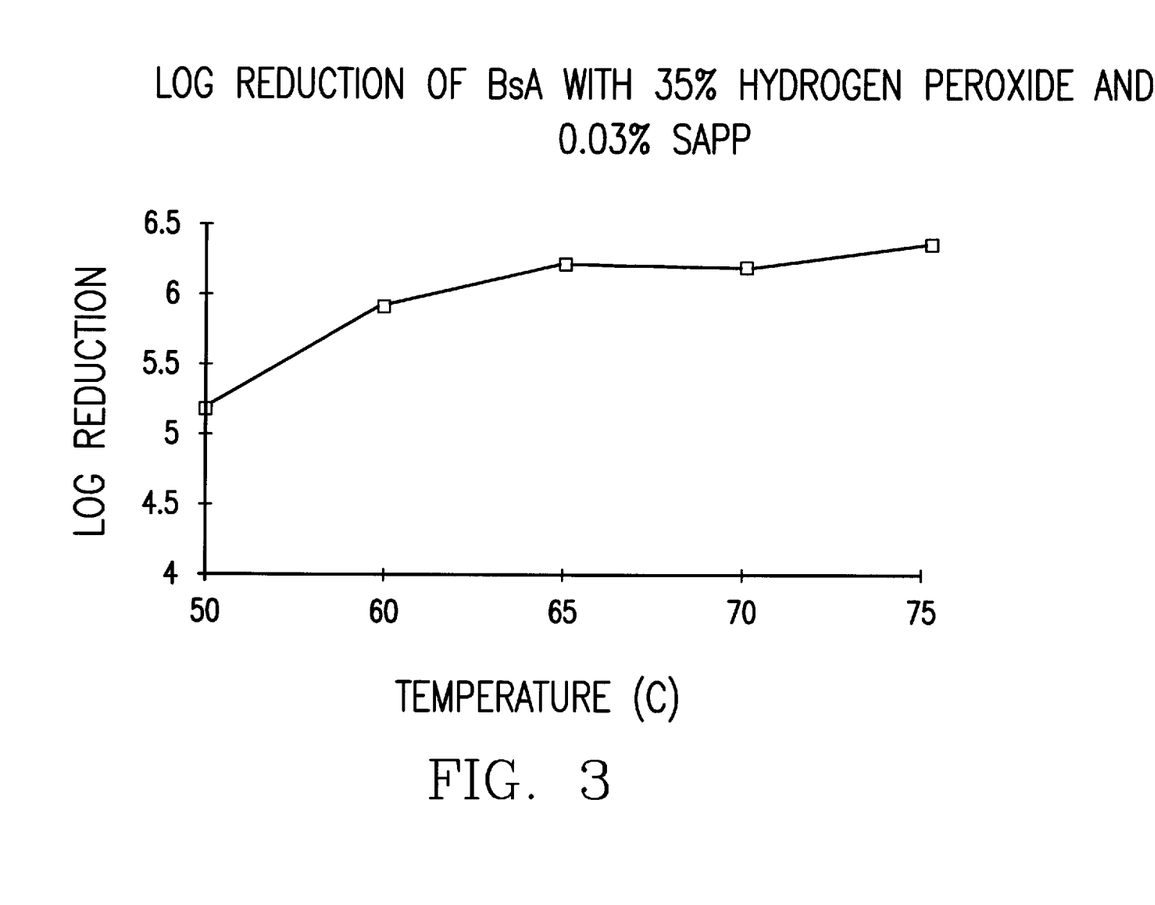
FIG. 3 is a plot of the destruction (log reduction) of *Bacillus subtilis* strain A (BsA) spores exposed for 6.6 seconds at varying temperatures to a conventional disinfecting solution contaning 35% by weight of hydrogen peroxide and 0.03% by weight of sodium acid pyrophosphate (SAPP).
Figure 4:
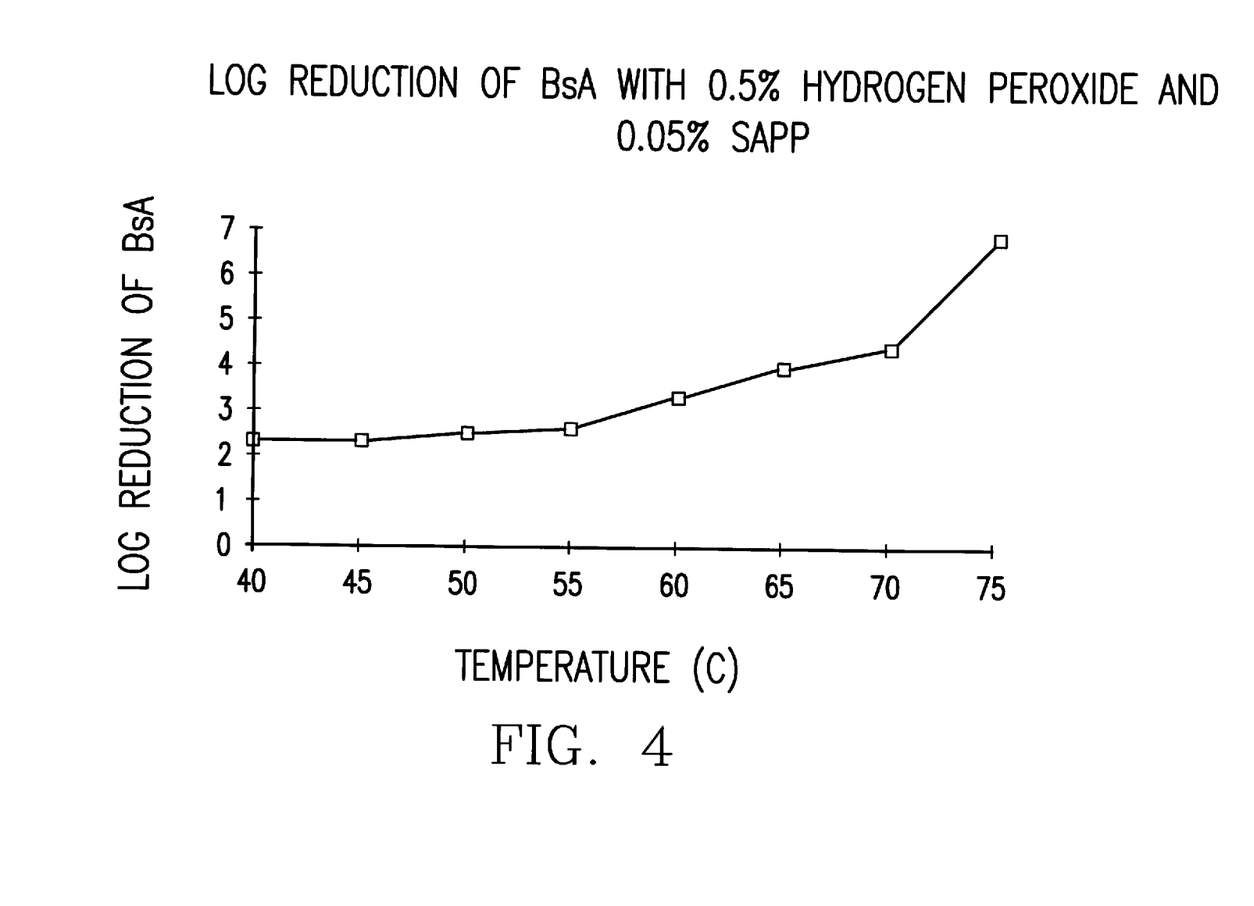
FIG. 4 is a plot of the destruction (log reduction) of *Bacillus subtilis* strain A (BsA) spores exposed for 30 minutes at varying temperatures to an improved disinfecting solution containing 0.5% by weight of hydrogen peroxide and 0.05% by weight of sodium acid pyrophosphate (SAPP).

FIG. 3 is a plot showing the destruction, in terms of log reduction, of *Bacillus subtilis* strain A (BsA) spores exposed for 6.6 seconds to varying temperatures of a conventional disinfecting solution containing 35% by weight of hydrogen peroxide and 0.03% by weight of sodium acid pyrophosphate (SAPP). FIG. 4 is a plot showing the destruction, in terms of log reduction, of *Bacillus subtilis* strain A spores exposed for 30 minutes to an improved disinfecting solution containing 0.5% by weight of hydrogen peroxide and 0.05% by weight of sodium acid pyrophosphate (SAPP). In FIGS. 3 and 4, a log reduction value of 1 means that the spore population has been reduced by a factor of 10; a log reduction value of 7 means that the spore population has been reduced by a factor of $10^7$. As shown in FIG. 3 for 35% $H_2O_2$/0.003% SAPP, the reduction of spores reaches a maximum at around 60°–75° C. FIG. 4 for 0.5% $H_2O_2$/0.05% SAPP shows that the reduction of spores using the improved disinfecting solution increases constantly as the temperature of the solution increases, showing neither a shoulder or tailing.

Machine Tests

Test Cycles

Cycle 2, a conventional disinfection cycle (water at 90° C. for 30 minutes followed by peracetic acid at 40° C. for 30 minutes), was compared to cycle 1, an improved disinfection cycle (0.1–1.0% $H_2O_2$/0.01–0.1% SAPP at 90° C. for 30 minutes followed by a cool water rinse).

Test Organisms

Spores of *Bacillus subtilis* var globigii and spores of *Bacillus stearothermophilus* were employed in the testing of the food contact surfaces of a food packaging machine. A suspension of *B. subtilis* estimated to be $1.5 \times 10^9$ spores/mL water was diluted in sterile 70% ethanol to produce approximately $1.5 \times 10^8$ colony forming units (cfus) per mL. A suspension of *B. stearothermophilus* estimated to be $1.7 \times 10^8$ spores/mL was extended with 100% ethanol to produce approximately $1 \times 10^8$ cfu/mL.

Machine Inoculation/Test Procedure

Figure 5:
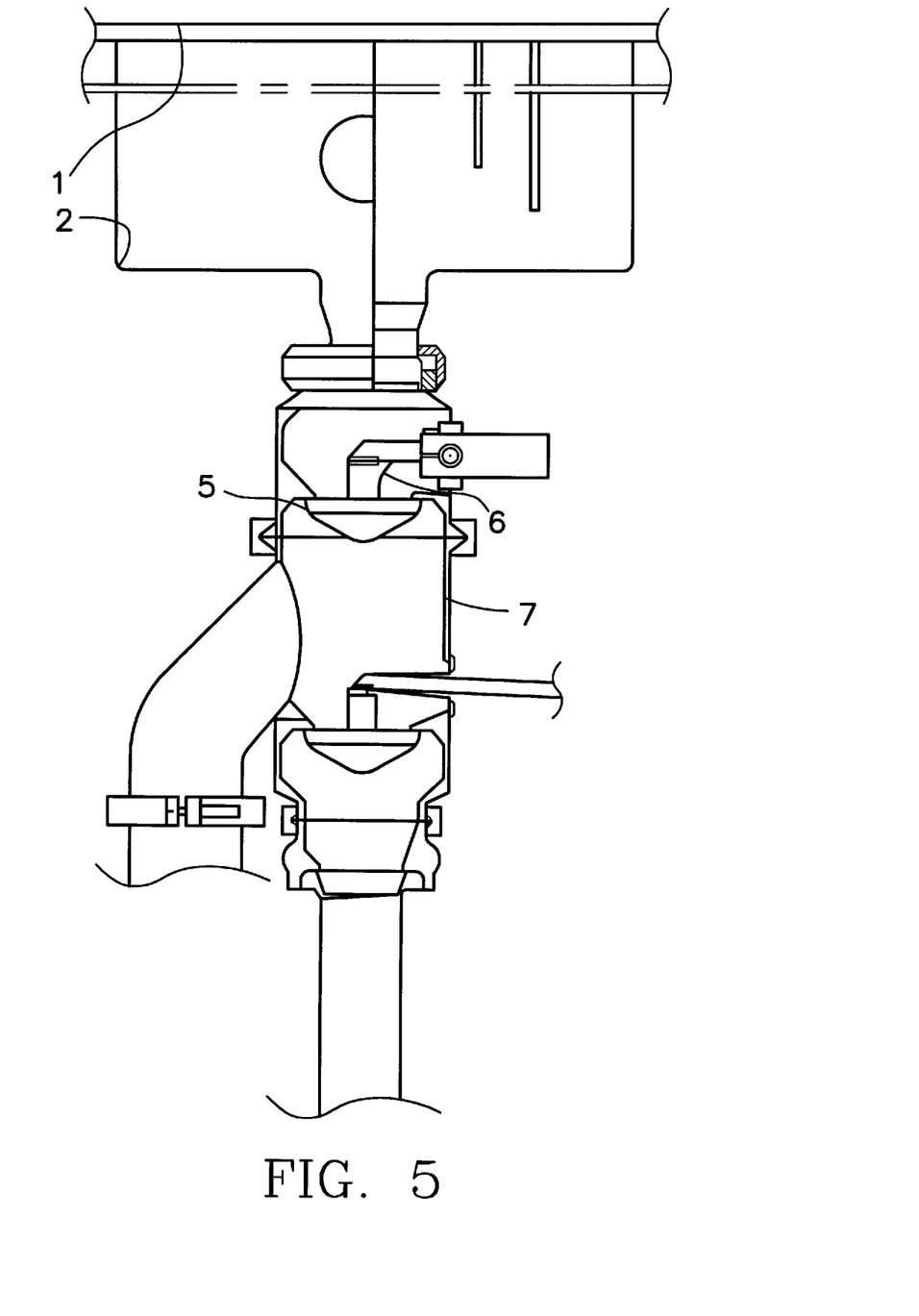
FIGS. 5, 6 and 7 are schematic diagrams of portions of a food packaging machine showing the locations at which test organisms were placed to test the efficacy of the improved method and solution described herein.
Figure 6:
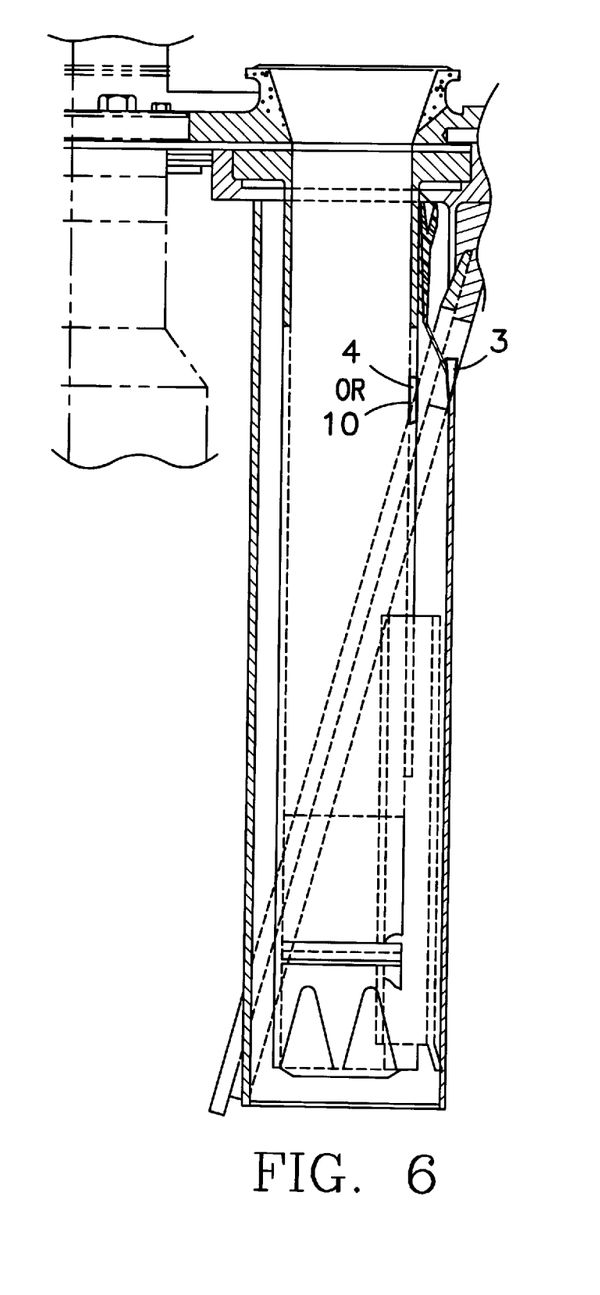
Figure 7:
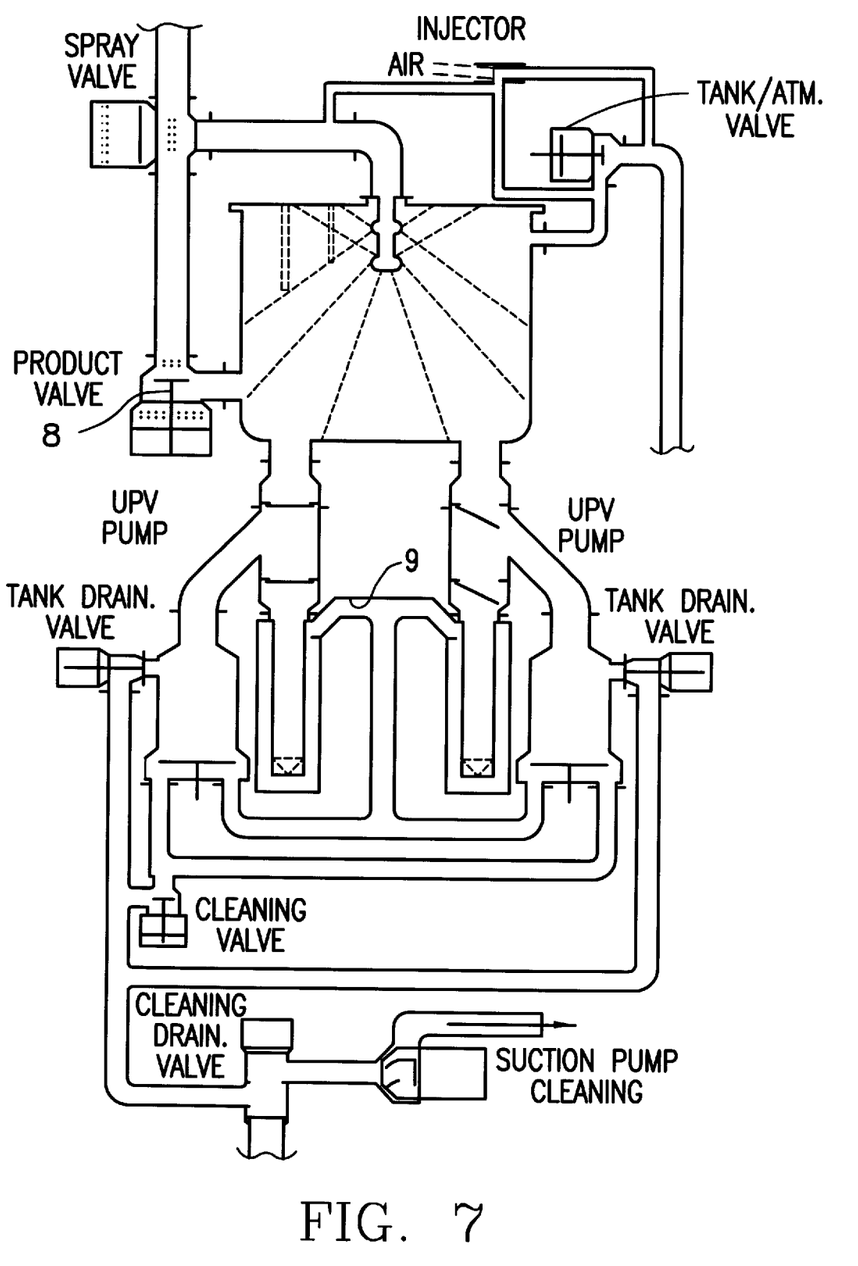

Ten test cites were chosen, each receiving both test organisms at separate locations. The ten test sites, schematically illustrated in FIGS. 4, 5 and 6, were as follows:
1. Top of filler tank (cover);
2. Corner of filler tank;
3. Cleaning box cover, fill tube 1;

4. Fill tube 1;
5. Upper universal product valve ("UPV");
6. Behind UPV;
7. Recharge chamber;
8. Product valve (inlet to tank);
9. Sterile air line;
10. Fill tube 2.

After cleaning of the machine, the ten sites were inoculated with approximately $10^6$ spores/spot of each organism by applying a 10 μl volume of each spore suspension to the inoculation site. Each spot was circled with indelible markers of two different colors to distinguish the two different test organisms being applied. The inoculum was allowed to dry completely. After drying, each site was swabbed using a sterile cotton-tipped swab moistened with 0.1% peptone water (excess water was pressed away). A standard swabbing pattern was employed. The swab was then broken off into 10 mL of 0.1% peptone water to be used to determine initial counts of organisms applied to the machine. The sites were then dried with a clean paper towel and reinoculated as above. In addition, the spore strips were placed in the Pall filter (single strips of each inoculum level for cycle 2). After complete drying of the inoculum, the machine was made operational and cycle 1 (0.1–1.0% $H_2O_2$/0.01–0.1% SAPP) was run. After completion of cycle 1, the machine was disassembled and the test sites were reswabbed as described above. The second swabs were used for final counts to determine log reductions. The spore strips were aseptically removed from the machine (one was lost in the machine during cycle 1; all were recovered during cycle 2) and transferred to dextrose tryptone broth (DTB). After swabbing, the test sites were dried with a paper towel and the entire process was repeated to test cycle 2 (peracetic acid).

Initial Swab Recovery and Recovery of Survivors

Swabs were transported in 0.1 % peptone to the test laboratory, where the swabs in peptone were first vortexed for two minutes at high speed setting. For determination of initial counts, from each tube 0.1 mL was pipetted into a 9.9 mL peptone blank. The *B. subtilis* var globigii was then heat shocked for 13 minutes at 80° C. After a rapid cool-down, *B. stearothermophilus* was heat shocked for 25 minutes at 100° C. After a rapid cool-down in ice water, 1 mL was plated in duplicate in dextrose tryptone agar ("DTA"), while an additional 1 mL was pipetted into a 9.0 mL dilution blank. From this 9.0 mL tube, 1 mL was plated in duplicate in DTA.

For determination of survivors, from each tube 1 mL and 0.1 mL volumes were plated in duplicate in DTA. No heat shock was employed because of the possible presence of injured organisms. However, in order to determine whether any spores of *B. stearothermophilus* could be detected by heat activation, the tubes from the recovery step were also plated after heat-shocking (25 minutes at 10° C.). After cool-down in ice water, 1 mL and 0.1 mL volumes of the heat shocked *B. stearothermophilus* were plated in duplicate in DTA.

The *B. subtilis* plates were incubated at 30° C. for two days, while the *B. stearothermophilus* plates were incubated at 55° C. for two days. The spore strips in DTB were incubated at 55° C. for two weeks.

Results

Tables 1 and 2 show the results from the first machine test using hydrogen peroxide as the sanitizing agent (cycle 1), for each of the test organisms. The recovered initial inoculum level per spot was very close to the target of 6 logs per spot for each organism. As shown in Tables 1 and 2, the actual recovered inoculum level ranged from 5.6 logs to 6.6 logs. Neither organism was recovered from any of the test locations after the sanitizing cycle was completed. All locations had an apparent log. reduction of 5.6 or better. However, it could not be determined whether the log reductions were due to the sanitizer or to a washing effect.

TABLE 1

*Bacillus stearothermophilus*

| Site | Initial #/Spot | Log | # Recovered | Log Reduction |
|---|---|---|---|---|
| 1 | $8.6 \times 10^5$ | 5.9 | 0 | >5.9 |
| 2 | $1.1 \times 10^6$ | 6.0 | 0 | >6.0 |
| 3 | $1.0 \times 10^6$ | 6.0 | 0 | >6.0 |
| 4 | $8.4 \times 10^5$ | 5.9 | 0 | >5.9 |
| 5 | $9.8 \times 10^5$ | 6.0 | 0 | >6.0 |
| 6 | $4.4 \times 10^5$ | 5.6 | 0 | >5.6 |
| 7 | $1.1 \times 10^6$ | 6.0 | 0 | >6.0 |
| 8 | $7.7 \times 10^5$ | 5.9 | 0 | >5.9 |
| 9 | $8.8 \times 10^5$ | 5.9 | 0 | >5.9 |
| 10 | $1.3 \times 10^6$ | 6.1 | 0 | >6.1 |

TABLE 2

*Bacillus subtilis* var globigii

| Site | Initial #/Spot | Log | # Recovered | Log Reduction |
|---|---|---|---|---|
| 1 | $2.2 \times 10^6$ | 6.3 | 0 | >6.3 |
| 2 | $1.5 \times 10^6$ | 6.2 | 0 | >6.2 |
| 3 | $3.2 \times 10^6$ | 6.5 | 0 | >6.5 |
| 4 | $2.4 \times 10^6$ | 6.4 | 0 | >6.4 |
| 5 | $7.8 \times 10^5$ | 5.9 | 0 | >5.9 |
| 6 | $1.3 \times 10^6$ | 6.1 | 0 | >6.1 |
| 7 | $2.7 \times 10^6$ | 6.4 | 0 | >6.4 |
| 8 | $3.4 \times 10^6$ | 6.5 | 0 | >6.5 |
| 9 | $3.7 \times 10^6$ | 6.6 | 0 | >6.6 |
| 10 | $2.2 \times 10^6$ | 6.3 | 0 | >6.3 |

Tables 3 and 4 show the results from the second machine test using peracetic acid (trade name Oxonia) as the sanitizing agent (cycle 2), for each of the test organisms. The recovered initial inoculum level per spot was very close to the target of 6 logs per spot for each organism. As shown in Tables 3 and 4, the actual recovered inoculum level ranged from 5.7 logs to 6.6 logs. Neither organism was recovered from any of the test locations after the sanitizing cycle was completed. The *B. subtilis* var. globigii recovery from location 6 was contaminated and therefore could not be analyzed. All other locations had an apparent log reduction of 5.9 or better.

TABLE 3

*Bacillus stearothermophilus*

| Site | Initial #/Spot | Log | # Recovered | Log Reduction |
|---|---|---|---|---|
| 1 | $1.2 \times 10^6$ | 6.1 | 0 | >6.1 |
| 2 | $1.2 \times 10^6$ | 6.1 | 0 | >6.1 |
| 3 | $1.1 \times 10^6$ | 6.0 | 0 | >6.0 |
| 4 | $1.1 \times 10^6$ | 6.1 | 0 | >6.1 |
| 5 | $1.3 \times 10^6$ | 6.1 | 0 | >6.1 |
| 6 | $9.7 \times 10^5$ | 6.0 | 0 | >6.0 |
| 7 | $1.4 \times 10^6$ | 6.1 | 0 | >6.1 |
| 8 | $8.7 \times 10^5$ | 5.9 | 0 | >5.9 |
| 9 | $1.3 \times 10^6$ | 6.1 | 0 | >6.1 |
| 10 | $8.0 \times 10^5$ | 5.9 | 0 | >5.9 |

TABLE 4

*Bacillus subtilis* var globigii

| Site | Initial #/Spot | Log | # Recovered | Log Reduction |
|------|---------------|-----|-------------|---------------|
| 1 | $2.3 \times 10^6$ | 6.4 | 0 | >6.4 |
| 2 | $2.7 \times 10^6$ | 6.4 | 0 | >6.4 |
| 3 | $1.9 \times 10^6$ | 6.3 | 0 | >6.3 |
| 4 | $2.2 \times 10^6$ | 6.4 | 0 | >6.4 |
| 5 | $3.4 \times 10^6$ | 6.5 | 0 | >6.5 |
| 6 | $5.0 \times 10^5$ | 5.7 | — | — |
| 7 | $2.8 \times 10^6$ | 6.4 | 0 | >6.4 |
| 8 | $4.0 \times 10^6$ | 6.6 | 0 | >6.6 |
| 9 | $3.2 \times 10^6$ | 6.5 | 0 | >6.5 |
| 10 | $3.1 \times 10^6$ | 6.6 | 0 | >6.5 |

Thus, an improved disinfection solution comprising 0.1–1.0% $H_2O_2$ and 0.01–0.1% SAPP exhibits sporicidal efficacy equivalent to that of peracetic acid. The improved disinfecting solution can be used in lieu of the acid ($HNO_3$ or $H_3PO_4$) wash, water rinse, and peracetic acid wash steps in traditional disinfecting methods (steps (d) through (g) above). In this regard, the presence of 0.01–0.1% SAPP in the improved solution stabilizes the hydrogen peroxide to prevent its decomposition, and the bidentate ligand binds cations like $Ca^{++}$, $Cu^{++}$, and $Fe^{++}$, to remove metal ions, rust and scale from the food contact surfaces.

Figure 8:
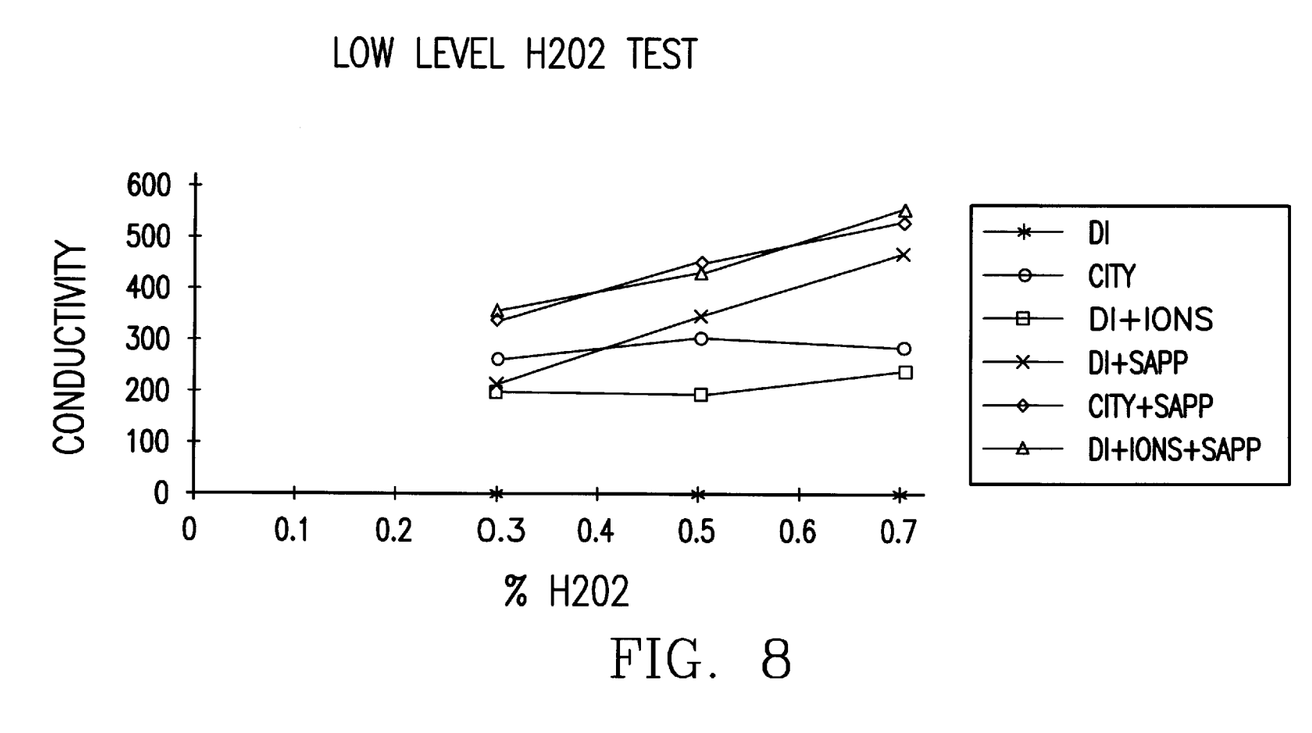
FIG. 8 is a plot of the effect of hydrogen peroxide concentration for various solutions on the conductivity.

Table 5 is a compilation of data for different solutions. The solutions are SAPP and hydrogen peroxide balanced with DI (deionized) Water, city water, or DI water plus ions (ferrous sulfate concentration of 100 ppm). The concentration of hydrogen peroxide was varied as well as the concentration of SAPP. As shown in FIG. 8, zero conductivity was measured for DI water alone. When SAPP was added to the DI water, the conductivity rose in relation to the increase in SAPP concentration. Similar increases are illustrated for city water and DI water plus ions. The greatest conductivity was measured for DI water plus ions with SAPP. Referring again to Table 5, the last row of DI water plus ions with a SAPP concentration lower than 100 ppm has a fairly constant conductivity. This suggests that the SAPP reacts with the ions reducing the overall conductivity. Above 100 ppm, the SAPP has reacted with all of the ions and thus demonstrates an increased conductivity. As mentioned above, the SAPP exhausts the supply of cations thereby removing the cations through precipitation from the solution and ultimately from the food contact surfaces.

Figure 9:
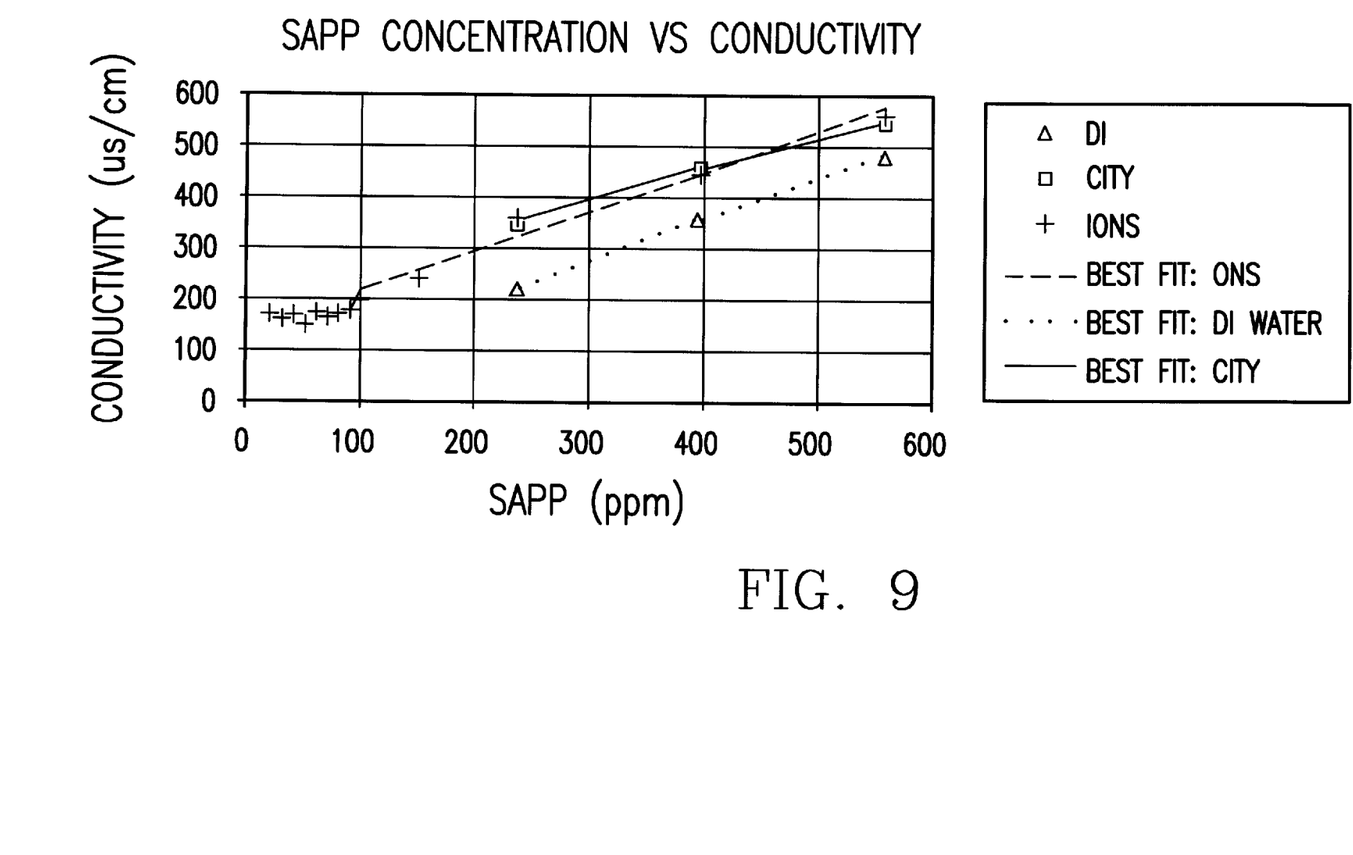
FIG. 9 is a plot of the effect of SAPP concentration on the conductivity.

FIG. 9 plots the change in conductivity versus the change in SAPP concentration, As the SAPP concentration is increased for DI water, city water and DI water plus ions, the conductivity is increased. In this manner, the SAPP concentration allows the solution to be monitored (through conductivity) in order to effect proper dosing of the solution. Of particular note is the exhaustion of the cations in the DI water plus ions example. This is illustrated in FIG. 9 where the concentration of SAPP is under 100 ppm. As shown, the conductivity remains constant until a sufficient amount of SAPP is added to the solution to exhaust the cations thereby allowing for increased conductivity.

The presence of 0.01–0.1 % SAPP in the improved solution also permits its detection by concentration monitoring and metering equipment, thus facilitating the automatic dosing of the $H_2O_2$/SAPP solution. By contrast, the trace amount of SAPP in the commercially available $H_2O_2$/SAPP solution (trade name pre-stabilized OXY-PAK) does not permit concentration monitoring and automatic dosing.

Finally, use of the improved disinfection solution comprising 0.1–1.0% $H_2O_2$ and 0.01–0.1% SAPP permits the direct transition of the machine to food product without the need for an intermediate rinse cycle. SAPP is an adjuvant substance generally recognized as safe in or on food. Residues of hydrogen peroxide and SAPP from the improved solution on the food contact surfaces, as well as on the packaging material and in the product itself, can be present without adverse effects on health and safety under 21 CFR 178.1005. Moreover, residues of hydrogen peroxide and SAPP from the improved solution have not been found to impart an off-flavor to products packaged following disinfection using the improved solution.

While particular elements, embodiments and applications of the present invention, have been shown and described, it will be understood, of course, that the invention is not limited thereto since modifications may be made by those skilled in the art, particularly in light of the foregoing teachings. It is therefore contemplated by the appended claims to cover such modifications as incorporate those features which come within the spirit and scope of the invention.

We claim as our invention:

1. A method of disinfecting the food contact surfaces of a food packaging machine, the method comprising:
   introducing to the machine an aqueous solution comprising from about 0.1% to about 1% by weight of hydrogen peroxide and from about 0.01% to about 0.1% by weight of sodium acid pyrophosphate;
   contacting the food contact surfaces with said solution at a temperature of at least about 70° C. for a time period of at least about 15 minutes; and
   removing substantially all of said solution from the machine.

2. The method of claim 1 wherein said contacting temperature ranges from about 90° C. to about 100° C.

3. The method of claim 1 wherein said contacting time period is at least about 30 minutes.

4. The method of claim 3 wherein said contacting time period is about 30 minutes.

5. The method of claim 1 further comprising, between steps (b) and (c):
   cooling said solution to room temperature within the machine while said solution remains in contact with the food contact surfaces.

6. The method of claim 5 wherein said solution is removed by introducing to the machine food to be packaged.

7. An aqueous solution for disinfecting the food contact surfaces of a food packaging machine, said solution comprising from about 0.1% to about 1% by weight of hydrogen peroxide and from about 0.01 % to about 0.1 % by weight of sodium acid pyrophosphate.

8. A solution for disinfecting the food contact surfaces of a food packaging machine, said solution consisting essentially of from about 0.1 % to about 1% by weight of hydrogen peroxide, from about 0.01 % to about 0.1% by weight of sodium acid pyrophosphate, and the balance water.

* * * * *